(12) United States Patent
Catt et al.

(10) Patent No.: US 6,235,241 B1
(45) Date of Patent: May 22, 2001

(54) READING DEVICES AND ASSAY DEVICES FOR USE THEREWITH

(75) Inventors: Michael Catt; Paul Henry Mundill; Michael Evans Prior, all of Northampton (GB)

(73) Assignee: Unipath Limited, Basingstoke Hampshire (GB)

( * ) Notice: Subject to any disclaimer, the term of this patent is extended or adjusted under 35 U.S.C. 154(b) by 0 days.

(21) Appl. No.: 09/078,501

(22) Filed: May 14, 1998

Related U.S. Application Data

(62) Division of application No. 08/338,141, filed on Nov. 9, 1994.

(30) Foreign Application Priority Data

Nov. 12, 1993 (EP) .................................................. 93309053

(51) Int. Cl.[7] .................................................. G01N 21/00
(52) U.S. Cl. ...................... 422/56; 422/82.05; 422/82.09
(58) Field of Search ............................. 422/82.05, 82.09, 422/61, 56, 57, 58; 356/432, 443

(56) References Cited

U.S. PATENT DOCUMENTS

| 4,717,545 | * | 1/1988 | Morris ..................................... 422/56 |
| 4,755,058 |   | 7/1988 | Shaffer . |
| 4,931,659 |   | 6/1990 | Sabater et al. . |
| 4,935,346 | * | 6/1990 | Phillips et al. ......................... 422/56 |
| 4,943,522 | * | 7/1990 | Eisinger et al. ......................... 422/56 |
| 5,179,005 | * | 1/1993 | Phillips et al. ......................... 422/56 |
| 5,281,395 | * | 1/1994 | Markart et al. ...................... 422/82.05 |
| 5,837,546 | * | 11/1998 | Allen et al. ......................... 422/82.09 |

FOREIGN PATENT DOCUMENTS

| 212599 |   | 3/1987 | (EP) . |
| 0283285 | * | 9/1988 | (EP) . |
| 291194 |   | 11/1988 | (EP) . |
| 383619 |   | 8/1990 | (EP) . |

OTHER PUBLICATIONS

JP 59–214768, Mochida Pharm.KK, Derwent Publication, 05/1983.
JP 63–134953, Shimadzu Seisakusho KK, Derwent Publication, 02/1988.

* cited by examiner

*Primary Examiner*—Elizabeth McKane
(74) *Attorney, Agent, or Firm*—Pillsbury Wintrop LLP

(57) ABSTRACT

An assay result reader, for use in conjunction with an assay device comprising a porous liquid-permeable carrier in the form of a strip or sheet through the thickness of which electromagnetic radiation is transmissible, the carrier including a detection zone in which an assay result is revealed by specific binding of a detectable material directly or indirectly to a binding agent immobilized in the detection zone, detection of the detectable material being effected by determining the extent to which electromagnetic radiation transmitted through the thickness of said carrier is attenuated by the presence of the detectable material bound in the detection zone.

19 Claims, 7 Drawing Sheets

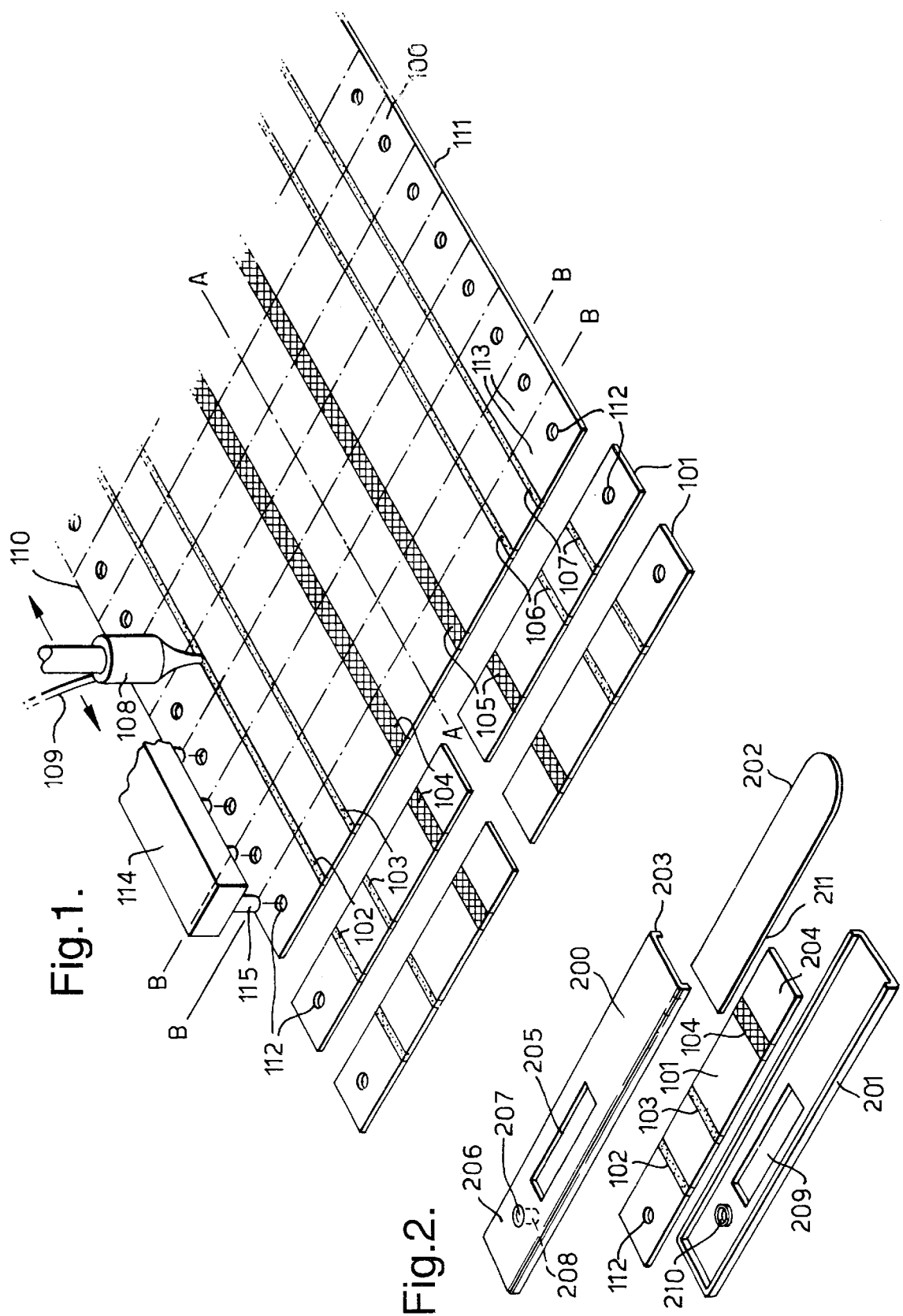

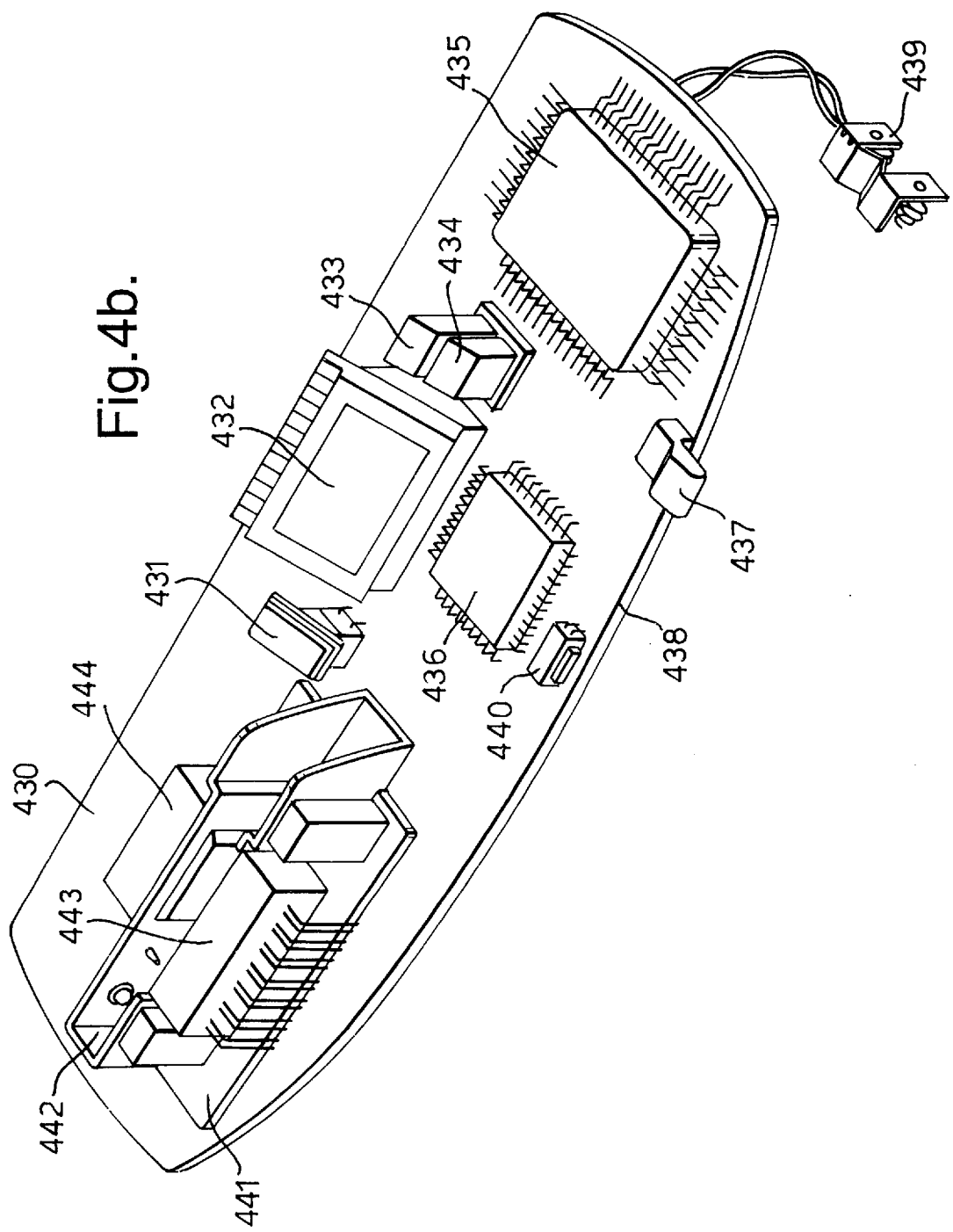

READING DEVICES AND ASSAY DEVICES FOR USE THEREWITH

This is a division of application Ser. No. 08/338,141, filed Nov. 9, 1994.

FIELD OF THE INVENTION

This invention relates to devices for reading the results of assays, to assay devices for use in conjunction with reading devices, and to methods using such devices.

An objective of the invention is to provide assay result reading devices and associated sample testing devices which can provide accurate quantitative assay information in a simple, quick and cost effective manner. Such devices can be used in a wide range of situations such as hospitals, clinics, doctors' offices, and the home. Depending on the circumstances, the analyte under investigation can also vary widely. Examples are infectious disease organisms or markers, metabolites in body fluids indicative of a change in the health or condition of a patient, and administrable or ingestable substances such as medicaments or drugs of abuse.

The invention is particularly, although not exclusively, concerned with assays which can be performed by comparatively untrained people and especially in the home.

BACKGROUND TO THE INVENTION

Home-use assay devices such as pregnancy tests are now well established. In the case of a pregnancy test, which merely needs to provide the user with a "yes/no" result, the technology now available enables the assay result to be read easily by eye without the need for any ancillary equipment.

Home-use assays are intended primarily to detect physiological changes in the human body, with the objective of promoting the health, general well-being or lifestyle of the individual. The consumer is becoming increasingly health conscious, and the ability of the consumer to monitor his or her bodily functions is being encouraged.

In some instances this can facilitate the interaction between the individual consumer and the medical profession (GP).

There are many assays indicative of physiological changes in the human body which currently can only be performed using sophisticated laboratory techniques. In order to provide useful information concerning the individual under test, such assays generally need to yield a result in precise numerical terms, eg. the concentration of a specific analyte in a body fluid.

Accordingly there is a need for an assay system, especially applicable to the testing of body fluid samples in the home, which combines convenience of sample testing together with simple and cost-effective numerical determination of the assay result.

Many assay devices are described in the technical literature with suggestions that the assay result can be read using optical equipment. The use of fluorescence emission, or light reflectance, is often suggested. Such techniques are mostly appropriate for use in sophisticated laboratories. In EP-A2-212599, which describes multizone analytical elements having a detectable signal concentrating zone, the suggestion is made that a detectable signal indicative of an assay result in the zone can be measured by electromagnetic radiation, such as light, transmitted through the zone. EP-A2-212599 indicates that the element can be made from porous fibrous materials, such as paper and nitrocellulose. However, no practical details are provided to indicate how an accurate measurement might be made using transmitted light.

SUMMARY OF THE INVENTION

By the invention, we have found that quantitative information can be derived by transmission reading of an assay strip or the like if the incident electromagnetic radiation is uniform across a region of the test strip which encompasses and extends beyond the test zone.

In one embodiment, the invention provides a method of "reading" the result of an assay effected by concentrating a detectable material in a comparatively small zone of a carrier in the form of a strip, sheet or layer through the thickness of which electromagnetic radiation, such as light, is transmissible, wherein at least a portion of one face of said carrier is exposed to incident electromagnetic radiation which is substantially uniform across the entire portion, said portion including said zone, and electromagnetic radiation emerging from the opposite face of said carrier is measured to determine said assay result.

PREFERRED EMBODIMENTS OF THE INVENTION

Preferably, the incident electromagnetic radiation is of substantially uniform intensity.

This uniformity can be achieved, for example, by providing a columated source of electromagnetic radiation, using conventional focussing means such as lenses and light guides to provide parallel incident electromagnetic radiation which falls essentially normally across the entire exposed portion of the carrier.

However, in a more preferred embodiment of the invention, the incident electromagnetic radiation is diffuse and bathes the exposed portion of the carrier uniformly in a randomly scattered manner.

In another embodiment, the invention provides an assay device comprising a porous liquid-permeable carrier strip or sheet through the thickness of which electromagnetic radiation is transmissible diffusely, said carrier being within a casing, said carrier including at least one detection zone in which an assay result is revealed by specific binding of a detectable material directly or indirectly to a binding agent immobilised in said detection zone, detection of said material being effected as a response to said electromagnetic radiation, and said casing having electromagnetic radiation transmitting regions enabling electromagnetic energy from an external source to be passed through said device, said detection zone lying in the electromagnetic radiation path between said electromagnetic radiation transmitting regions.

Preferably, the porous carrier strip or sheet comprises paper, nitrocellulose or the like, preferably of a thickness not exceeding 1 mm.

In yet another embodiment, the invention provides an assay device and assay result reader combination, wherein:

a) said device comprises a porous liquid-permeable carrier strip or sheet through the thickness of which electromagnetic radiation is transmissible diffusely, said carrier preferably being within a casing or cover, said carrier including at least one detection zone in which an assay result is revealed by specific binding of a detectable material directly or indirectly to a binding agent immobilised in said detection zone;

b) said casing or cover, if present, has electromagnetic radiation transmitting regions enabling electromagnetic radiation from an external source to be passed through said device, said detection zone lying in a path between said transmitting regions;

c) said assay result reader has receiving means for receiving at least a portion of said device, said portion including said detection zone to present said detection zone to reading means, said reading means incorporating a source of uniform electromagnetic radiation and one or more sensors located such that upon insertion of said device into said receiving means, electromagnetic radiation can be passed through said device and the intensity of electromagnetic radiation emerging from said device can be detected by said sensor(s).

Preferably, said receiving means incorporates interlocking means engagable with corresponding interlocking means on said device to ensure that upon receipt of said device by said reader said detection zone(s) is located and maintained in a predetermined spacial relationship relative to said reading means.

Preferably, said receiving means includes actuating means triggered by said receipt of said device, said actuating means causing said reading of said detection zone(s) to be initiated.

If the assay device is provided with a casing, it is advantageous if said device casing includes internal registration means which engages with corresponding registration means associated with said carrier such that said detection zone within said device casing is located in a predetermined spacial relationship relative to said registration means on said device casing. Preferably, said internal registration means comprises a pin or the like, engagable with a hole, indentation of the like in said carrier, said detection zone being at a predetermined location on said carrier relative to said hole or indentation.

During manufacture of said assay device, said corresponding registration means may be used to facilitate or control accurate formation, e.g. by means of reagent printing techniques, of said detection zone on said carrier. In addition, or alternatively, accurate placement of said carrier within said device casing can be facilitated or controlled by said registration.

In a further embodiment, the invention provides an assay result reader, for use in conjunction with an assay device comprising a porous liquid-permeable carrier strip or sheet through the thickness of which electromagnetic radiation is transmissible, said carrier including a detection zone in which an assay result is revealed by specific binding of a detectable material directly or indirectly to a binding agent immobilised in said detection zone, detection of said material being effected as a response to said electromagnetic radiation, said assay result reader comprising:

a) receiving means for receiving at least a portion of said assay device, said portion including said detection zone;

b) reading means associated with said receiving means, said reading means comprising:

i) at least one source of uniform diffuse (preferably electromagnetic radiation; and ii) one or more sensors capable of detecting the intensity of said electromagnetic radiation;

said source and said sensor(s) being positioned such that when said portion of said assay device is received within said receiving means, said detection zone is disposed in a path between said source and said sensor(s).

The assay device/reader combination can be supplied to the consumer as a single test kit. In general however, whereas the reader will be a relatively permanent unit which the consumer can use time and again (and which may be provided with an electronic memory/data-processing facility which enables the results of many sequential assays to be evaluated) the testing devices will be intended for use only once and thereafter will be discarded. Accordingly, the test devices may be supplied to the consumer separately from the reader, e.g. in multi-packs.

By ensuring precise interlocking between the testing device and the reader, and also ensuring precise registration of the location of the detection zone within the testing device itself, the testing zone will be presented to the reader in a constant pre-determined position every time a testing device is inserted into the reader. The construction of the optical system within the reader (light source and sensors) can therefore be kept as simple as possible, because it is not essential for the sensors to include any scanning facility, for example, which would otherwise be required if the exact location of the detection zone was not known. By avoiding the need for a sophisticated optical reading system, the cost of the reader/monitor may be reduced. Simplification of the optical reading system may also enable the reader/monitor to be of small size which will assist convenient and unobtrusive use in the home. Of course, a scanning facility can be included in the reader if desired.

An additional benefit of providing an internal registration system which ensures precise location of the detection zone within the test device, is that automated manufacture and quality control of the testing devices can be facilitated. Because it is envisaged, for example, in the case of an ovulation cycle monitor, that the consumer will need to use several testing devices each month, the testing devices may need to be manufactured in large numbers at low cost. Internal registration can facilitate automated manufacture and high throughput.

In principle, any electromagnetic radiation can be used to effect the transmission measurement in the invention. The electromagnetic radiation should preferably be capable of being rendered diffuse. Preferably the electromagnetic radiation is light in the visible or near-visible range. This includes infra-red light and ultra-violet light. It is generally envisaged that the detectable material used as a label in the assay is one which will interact with light in the visible or near visible range, eg. by absorption. The wavelength of the electromagnetic radiation chosen is preferably at or near a wavelength which is strongly influenced, eg. absorbed, by the label. For example, if the label is a substance which is strongly coloured, ie. visible to the naked human eye when the material is concentrated, the ideal electromagnetic radiation is light of a complementary wavelength. Particulate direct labels, for example, metallic (eg. gold) sols, non-metallic elemental (e.g. Selenium, carbon) sols, dye sols and coloured latex (polystyrene) particles are ideal examples. For instance, in the case of blue-dyed latex particles, the ideal electromagnetic radiaation is visible red light which will be strongly absorbed by the blue particles.

In a preferred embodiment of the invention, the transmitted electromagnetic radiation reaching the sensor(s) should be diffuse. The diffuseness may arise as a consequence of transmission of the electromagnetic radiation through the carrier strip or sheet, but more preferably is contributed by the source of the electromagnetic radiation emitting the energy in a highly diffuse form. In a preferred embodiment of the invention the source produces highly diffuse radiation and the carrier strip or sheet through which this radiation subsequently is transmitted is in comparative terms a much weaker diffuser.

A primary advantage of the use of diffuse light or other radiation in the context of the invention is that the reading of the assay result is much less likely to be adversely influenced by blemishes or contaminating material on the assay device. For example, dirt or scratches on the assay device in the region through which the radiation must be transmitted could strongly interfere with the accuracy of the determined result if focussed rather than diffuse light is used. By the use of a diffuse light source in accordance with the invention, it is possible to provide an assay result reader which can accurately interpret the result of an assay conducted even in an essentially transparent assay device without the assay result being adversely affected by minor contamination or damage (eg. superficial scratches) to the assay device.

In a preferred embodiment of the invention, the electromagnetic radiation from the source is pulsed. By synchronising the detectors (sensors) so that they function only in phase with the pulsed radiation source, it is possible to eliminate any background interference that might be caused by external radiation, e.g. ambient light. It is envisaged that the assays will mostly be conducted under circumstances of natural daylight or, even more often, artificial light. Artificial light is usually of a pulsed nature (typically 50–100 Hz) caused by the alternating nature of electricity supplies. By adopting a pulsed radiation source for the illumination of the assay device within the reader, the intrusion of natural daylight can be ignored. By selecting the pulse frequency such that it is sufficiently different from the prevailing artificial light, any interference due to artificial light can also be avoided. Preferably the pulse frequency of the energy should be at least about 1 kHz. An ideal pulse frequency is about 16 kHz. The electronics necessary to achieve synchronous pulsed sensing are familiar to those skilled in the art.

The use of pulsed light is very advantageous because it renders it unnecessary for the monitor to be "light tight". Not merely does this simplify the construction of the monitor but the reading of the assay result can be performed while the monitor is "open", thus simplifying the operation for the user.

The source of light or other electromagnetic radiation can comprise entirely conventional components. Ideal examples are commercially available LED's, preferably chosen to give a suitable wavelength of light that is strongly absorbed by the detectable material concentrated in the test zone(s). Light from the LED's should be passed through a strong diffuser before reaching the assay device. If desired, an array of LED's which are energised in turn can be used.

Suitable diffusers can be made, for example, from plastics materials, and are available commercially. If necessary, the light-scattering properties of the diffusing material can be enhanced by including particulate materials such as Titanium dioxide and Barium sulphate. An ideal diffusing material comprises polyester or polycarbonate, containing Titanium dioxide. A good inclusion level for the particulate material is at least about 1% by weight, preferably about 2%. By the use of a diffuser, all relevant regions of an assay strip may be measured simultaneously, and differences in light output from the source are eliminated.

The sensor(s) to detect emergent light can be conventional components such as photodiodes, e.g. silicon photodiodes.

Preferably, a second diffuser, which can be made from the same material as the primary diffuser, is located in front of the sensor(s). This ensures that the view seen by the sensor is not affected by the presence or absence of a test strip in the reading head. In consequence, the monitor can be calibrated in the absence of a test strip, and then measure an assay result in the presence of an assay strip.

By employing a uniform light source in accordance with the invention, it is possible to provide a reading system for test strips and the like which is relatively tolerant to variation in the placement of the test zone(s) from one strip to another, in the absence of a scanning sensor. Further benefits are obtained if test zone placement is controlled, as described herein.

For the purposes of enhancing the likelihood of conception, assay devices have already been marketed which enable the user to monitor the urinary concentration of lutenizing hormone (LH) which peaks sharply approximately one day in advance of ovulation. Daily testing of urinary LH concentration is conducted, for example using "dipstick" technology with the assay result being provided by a coloured end point, the intensity of the colour being proportional to LH concentration. By providing the consumer with a colour chart which enables the daily result to be compared against a standard, the "LH surge" can be detected simply by eye. Unfortunately, the monitoring of LH concentration is a very rare example of an assay relying on semi-quantitative data which is ameniable to such simple technology, being possible only because in relative concentration terms the LH surge is such a dramatic event. For most other potentially useful assays the analyte concentration changes in body fluids are much more subtle and only detectable accurately by instrumental means.

A need therefore exists to extend the currently available qualitative home-use testing technology into the area of precise quantitative testing. A convenient example, which is a logical extension of the present consumer interest in home-use pregnancy testing and ovulation prediction testing, is the extension into accurate monitoring of the ovulation cycle, not merely to enhance the likelihood of conception but indeed to provide reliable information for the purposes of contraception. Proposals have been made to analyse body fluids with this objective in mind. A common theme is to monitor periodic fluctuations in various hormone metabolite levels in urine.

The invention can be used in the determination of any body fluid analyte, especially in the monitoring of the human ovulation cycle by the determination of one or more hormones or metabolites thereof in body fluid, such as urine, for example either LH and/or estrone-3-glucuronide (E3G).

Within the preferred context of the present invention it is envisaged that a home-use sample liquid testing device will include a porous carrier material, such as a strip, through which applied sample liquid such as urine can permeate and wherein the assay result occurs by means of specific binding of a detectable material in a precisely-defined region (detection zone) of the carrier, such as a narrow line or small dot, containing an immobilized specific binding reagent. The invention is therefore concerned with ways in which localisation of a detectable material in such a detection zone can be determined accurately in a simple and cost-effective manner. Home-use devices for the analysis of urine, for example in pregnancy tests and ovulation prediction tests, are now widely available commercially. Many such devices are based on the principles of immunochromatography, and typically comprise a hollow casing constructed of plastics material containing a porous assay strip carrying pre-dosed reagents. The reagents within the device may include one or more reagents labelled with a direct label, such as a dye sol, a metallic (e.g. gold) sol, or a coloured latex (e.g. polystyrene) microparticle, which are visible to the eye when concentrated in a comparatively small test area of the strip. The user merely needs to apply a urine sample to one part of the casing to initiate the assay. The assay result becomes visible by eye within a few minutes without further action by the user. Examples of such devices are described in EP-A-291194 and EP-A-383619, the disclosures of which are incorporated herein by reference. Sample collection is conveniently achieved by means of a bibulous member which forms part of the device and which can readily take up sample liquid, e.g. from a urine stream. Optionally the bibulous member can protrude from the casing of the device to facilitate sample application.

Other embodiments of the invention, which will be apparent from the following detailed description, include assay devices for use as part of the reader/assay device combination, methods of manufacturing such assay devices, and methods of use of such assay devices and readers.

BRIEF DESCRIPTION OF THE DRAWINGS

By way of example only, assay devices and readers in accordance with the invention will now be described with reference to the accompanying drawings, of which:

FIG. 1 shows a general view of a sheet of porous material, e.g. paper, during the course of reagent deposition on the sheet and sub-division of the sheet into assay strips.

FIG. 2 shows an "exploded" view of an assay device of the invention incorporating an assay strip made as shown in FIG. 1.

FIGS. 4a, 4b and 4c show in partially "exploded" form the main features of a complete monitor in accordance with the invention, namely:

FIG. 4a: the lid and upper half of the casing;

FIG. 4b: an electronic circuit board incorporating a reading head;

FIG. 4c: the lower half of the casing and associated battery container.

Referring to FIG. 1, the sheet 100 of porous material, e.g. nitrocellulose, is intended to be divided into a plurality of identical assay strips 101 by cutting along central axis A—A and the lateral axes B—B.

Figure 3:
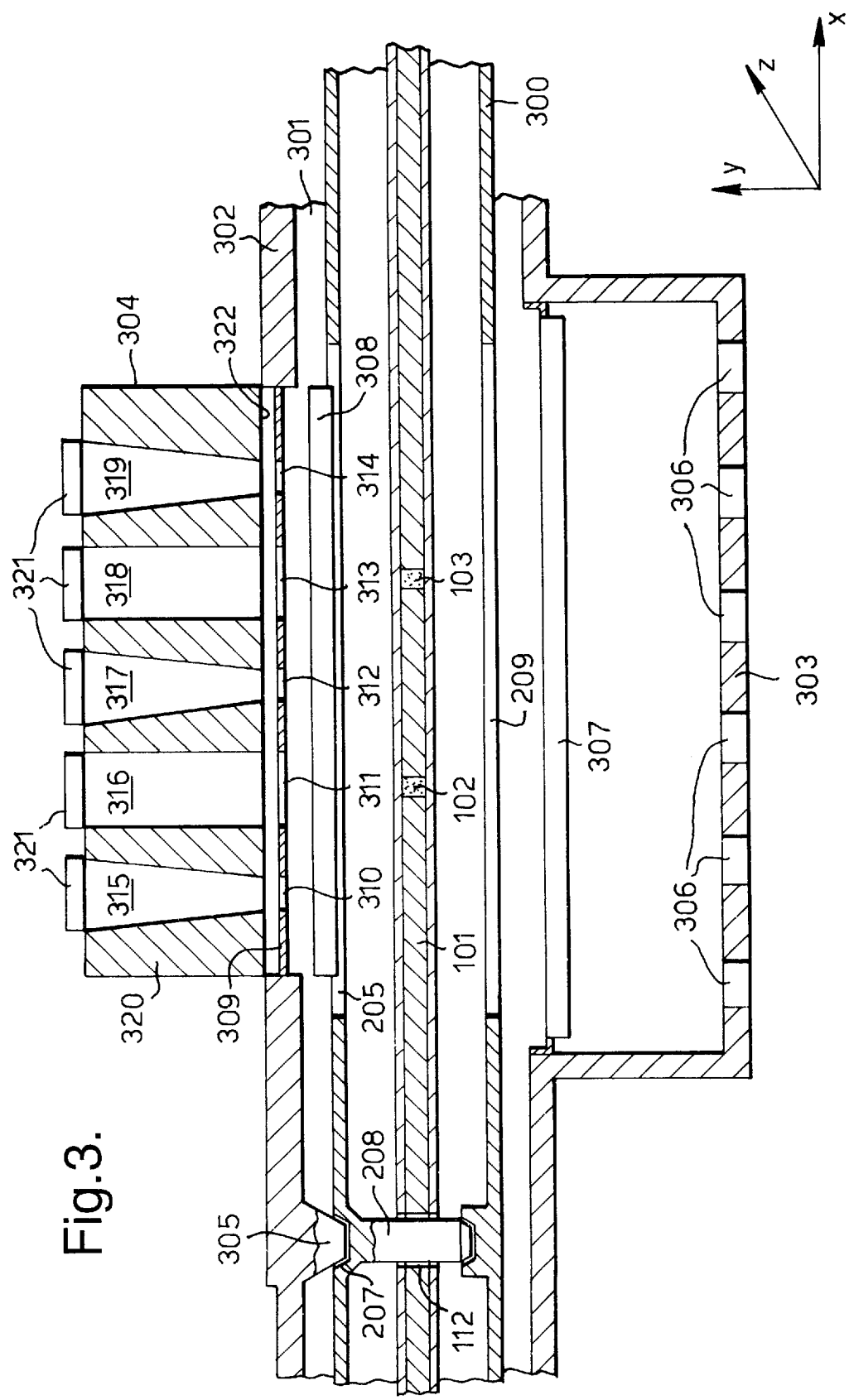
FIG. 3 shows in diagramatic cross-section an assay device of FIG. 2 located within the reading head of a monitor in accordance with the invention, working by light transmission through the assay strip. The y axis is distorted to show the arrangement of components.

Parallel lines (102–107) of assay reagents are placed on sheet 100 prior to sub-division. For the purposes of example only, the reagents are assumed to be a first immobilised antibody in lines 102 and 107, and a second different immobilised antibody in lines 103 and 106. Reagent deposition can be by means of a "pen" 108 or the like operated on a computer-controlled "x-y" plotting mechanism (not shown) and fed with appropriate buffered reagent solution via a metered flexible tube 109. If the material of sheet 100 is nitrocellulose, reagents such as antibodies and antigens can be immobilised by simple direct application onto the nitrocellulose, followed by blocking of the sheet material, for example with albumen or polyvinyl alcohol. Following reagent deposition and blocking, two lines 104 and 105 of mobile labelled reagent, such as antigen (e.g. E3G) or another antibody (e.g. anti-LH) labelled for example with a particulate direct label such as coloured latex, can be deposited. This deposition can be for example by means of another pen (not shown). Alternatively, the labelled reagent(s) can be held in a separate porous pad or the like, rather than being applied directly to the test strip material.

In order to achieve precise location of the reagent-containing lines, each longitudinal periphery 110, 111 of sheet 100 is pierced with a plurality of identical small holes 112 each one being situated within the width of a designated strip 113. Holes 112 are made in sheet 100 prior to the deposition of any reagents. The untreated sheet is located on a frame (not shown) or similar operating surface by means of a bar 114 pressed downwardly onto each lateral periphery of the sheet. Only one of these bars is (partially) shown. Each bar has a plurality of downwardly projecting pins 115, each of which locates precisely into one of the holes 112. The tracking of the reagent-depositing pen 108 is registered precisely with the position of the bars holding the sheet, and accordingly the reagent deposition is made in a predetermined precise line relative to the perforations in the sheet.

Following all necessary reagent depositions and other treatments of the sheet, the sheet is subdivided by cutting means (not shown) into individual identical strips 101. Each individual strip therefore contains one locating hole 112 with two reagent-containing lines or reaction zones (e.g. 102 and 103) located relative to hole 112 in precise predetermined positions extending across the width of each strip. At a location remote from hole 112 is a region (e.g. 104) of the strip bearing the mobile labelled reagent. The exact position of the labelled reagent relative to the hole is not necessarily as critical as the location of the reaction zones.

By way of example only, the individual strips will typically have a length of about 40 mm to about 80 mm, and a width of about 5 mm to about 10 mm, as is already conventional in the assay device art. A reagent-containing detection zone such as the reaction zones 102 and 103, will typically be a line of width about 1 mm running laterally across the strip. A small dot, e.g. circular with diameter of about 1 mm to about 3 mm, is an alternative. The detection zone is therefore only a relatively small proportion of the total area of the strip. If appropriate for the purposes of the assay, multiple detection zones containing the same or different reagents can be placed on each strip. This may necessitate more than one labelled component being used; multiple mobile labelled components can be placed upstream on the strip or elsewhere within the device (eg. in a sample application pad or wick, as described below).

Referring to FIG. 2, an assay device of the invention comprises a plastic casing having upper and lower halves 200 and 201 adapted to contain the assay strip 101 and also a bibulous sample receiving member 202 which can extend out of one end 203 of the assembled casing. In the assembled device the bibulous receiving member 202 overlaps the end 204 of the assay strip adjacent to the deposited labelled reagent. The upper half 200 of the casing includes a window or aperture 205 through which both detection zones 102 and 103 can be observed from outside the casing. Upper half of the casing contains on its external surface 206 a circular depression 207 on the central longitudinal access of the casing a short distance beyond the observation window relative to the end 203 of the casing accommodating the sample receiving member. On the inside of the upper half of the casing is a downwardly extending pin or peg 208 located directly below depression 207. The diameter of the downwardly extending pin or peg 208 matches that of the hole 112 in the assay strip 101, so that the strip can be positively located within the assembled device on the peg.

Lower half 201 of the casing also includes a light-transmitting window or aperture 209 which, in the assembled device, lies directly opposite to the result window 205 in the upper half of the casing. Lower half of the casing also contains a depression 210 which can accommodate the bottom end of the pin or peg 208 when the two halves of the casing are placed together to make an enclosure.

In the assembled device, the act of enclosing the strip and bibulous member between the upper and lower halves of the casing causes the overlapping portions 204 and 211 of the strip and bibulous member to be crimped together to provide a good moisture-conductive junction.

It is generally envisaged that the material of the casing will be opaque, e.g. white or coloured plastics material, but the casing can be translucent or indeed transparent if desired.

Referring to FIG. 3, the assay device 300 is seen located within a slot 301 in a monitor 302. This region of the assay device includes the two opposing windows 205 and 209.

The casing of the monitor is slotted to receive the portion of the assay device incorporating the result windows. On opposing sides of the slot is a light source 303 and a reading head 304.

The slot incorporates a button or projection 305 which can fit into the depression 207 on the external face of the casing of the assay device. Precise positive location of the casing within the slot is therefore achieved. Because the depression is in a fixed position relative to the internal pin or peg 208 within the assay device, and hence the registration hole 112 in the assay strip 101, the two detection zones 102 and 103 on the strip are located in a precise position relative to the reading head. The hole in the assay strip therefore acts as a positive reference throughout the manufacture of the assay device and ensures that after the device has been used and presented to the monitor the detection zones on the strip will be in the same position relative to the reading head each time. Accordingly there is no need for the reading head to incorporate a scanning facility to locate the detection zones in each presented device.

The light source or illuminator 303 incorporates a plurality of LEDs 306 to generate light, and this shines onto the assay strip via a diffuser 307 and the observation window 209 in the lower half of the assay device casing. The light passes through the thin nitrocellulose strip 101 and exits the assay device through the result window 205 in the upper half of the casing. Immediately outside window 205 is a second diffuser 308. After passing through the second diffuser 308, the light encounters a plate 309 having a plurality of apertures 310–314. There are five apertures in total, two of which (311, 313) are adjacent to the detection zones and the others (310, 312 and 314) lie in positions on either side of these detection zone apertures. The apertures are of slit form corresponding to the detection lines on the strip. The width of each of the two apertures 311 and 313 corresponding to the detection zones themselves is double the width of each of the three other apertures, which act as controls.

The light passing through these apertures travels down a corresponding slot 315–319 in a baffle plate 320. At the far end of each slot is a light detector 321. The detectors 321 are of identical size and specification. At the front face 322 of the baffle plate 320, each slot is of the same size as the corresponding aperture. At the rear face of the baffle adjacent to the light detectors each slot is of the same size as the face of the light detector adjacent to it. Accordingly, the two slots (316, 318) associated with the detection zone apertures are parallel-sided. The three slots (315, 317 and 319) associated with the control apertures increase in size as they progress towards the light detector.

The slot in the monitor can also accommodate gripping or biasing means such as one or more spring-loaded plates or pins (not shown) to further enhance the positive location of the assay device within the slot.

Ideally, the same optical signal is derived from each aperture irrespective of the precise line position opposite the apertures. The apertures can be of different sizes to promote this objective. The dimensions of the reference zone should be chosen to correspond as closely as possible with the actual area of the detection zone on the strip.

To reduce the possibility of cross-talk between the apertures, the assay strip should be held as close as possible to the apertures when the assay device is located in the slot in the monitor.

As described above, there are five optical measurement channels in the reading device. In addition, there can be a sixth electronic reference channel that provides calibration of the electronic gains in the detector circuitry.

A typical test strip may exhibit a gradient of detectable label concentration along its length, against which the detectable label at a reaction zone must be measured. To accommodate this measurements are ideally made either side of the reaction zone on the test strip. The signal from the reaction zone can be expressed as a ratio of the total signal recorded from the two adjacent reference areas on the strip.

The five measurement channels are divided into two reaction zones and three reference zones. One reference zone, located between the two reaction zones provides a reference optical measurement to both reaction zone measurements.

A reflectance measuring system must all be mounted on one side of the test strip. To achieve the same level of compactness for a five channel reading device would require the use of (relatively) expensive custom components. A transmission design can be made entirely from commercially-available, high volume optoelectronic components, facilitating the production of a monitor that is compact and relatively cheap.

The five detectors 321 are mounted on the back face of a baffle plate. Each detector views the test strip through an aperture in the baffle. The baffle prevents light viewed through one aperture from falling on adjacent detectors, and also provides accommodation for line placement tolerance. The position of the test zone within the field of view of a detector may vary from one edge of the aperture to the other in the x-axis. Any variation in the signal arising from this effect is a function of the angular displacement relative to the centre of the measuring detector. The depth of the baffle can be chosen to control the possible angular displacemen t of the test zone with respect to the detector, and to maintain the accuracy of the reading.

The projection 305 is maintained in precise location with respect to the apertures. The reference pin locates into depression 207 in the test device casing. This depression is also precisely located with respect to the internal pin 208 moulded into the test device, on which the test strip is located by it's own locating hole punched through the strip. The reaction zones are precisely located with respect to the locating hole. In this manner, within manufacturing tolerances, the reaction zones are held in precise positions with respect to the apertures through which the detectors view the test strip.

The iluminator can consist of a series of LEDs embedded in or placed behind a diffusing medium which provides a uniform and diffuse illumination of the test strip covering the reference and signal zones.

The incorporation of a diffuser between the apertures and the test strip is beneficial for calibration purposes. In order to calibrate each of the optical channels in the absence of the test strip it is highly desirable that each detector is collecting light from the same areas of the illuminator as is the case when a test device is present. The diffuser can be selected to be the dominant diffuser in the optical path so that the introduction of the test strip does not contribute signifiantly to changes in the illumination distribution observed by the detectors. In addition, the diffuser element can enable the optical assembly to incorporate a 'wipe clean' surface, desirable for long-term repeated performance of the optical assembly. By modulating the intensity of the illuminator, the optical channels can be calibrated, without the aid of moveable parts, 'invisibly' to the user prior to the insertion of a test device.

The test strip can consist of an optically diffuse layer of nitrocellulose or the like, preferably sandwiched between two layers of optically clear film, e.g. of polyester such as "Mylar". The clear film protects the nitrocelluose within which the assay reactions take place. Making reflectance measurements through thin transparent films is particularly difficult because of problems arising from specular reflections. Transmission measurement allows the optics to be constructed orthogonal to the measuring suface and minimises the adverse effects of reflection.

The invention is particularly applicable to the reading of test strips made of nitrocellulose and similar diffuse membranes that preferably do not exceed about 1 mm thickness.

Figure 4A:
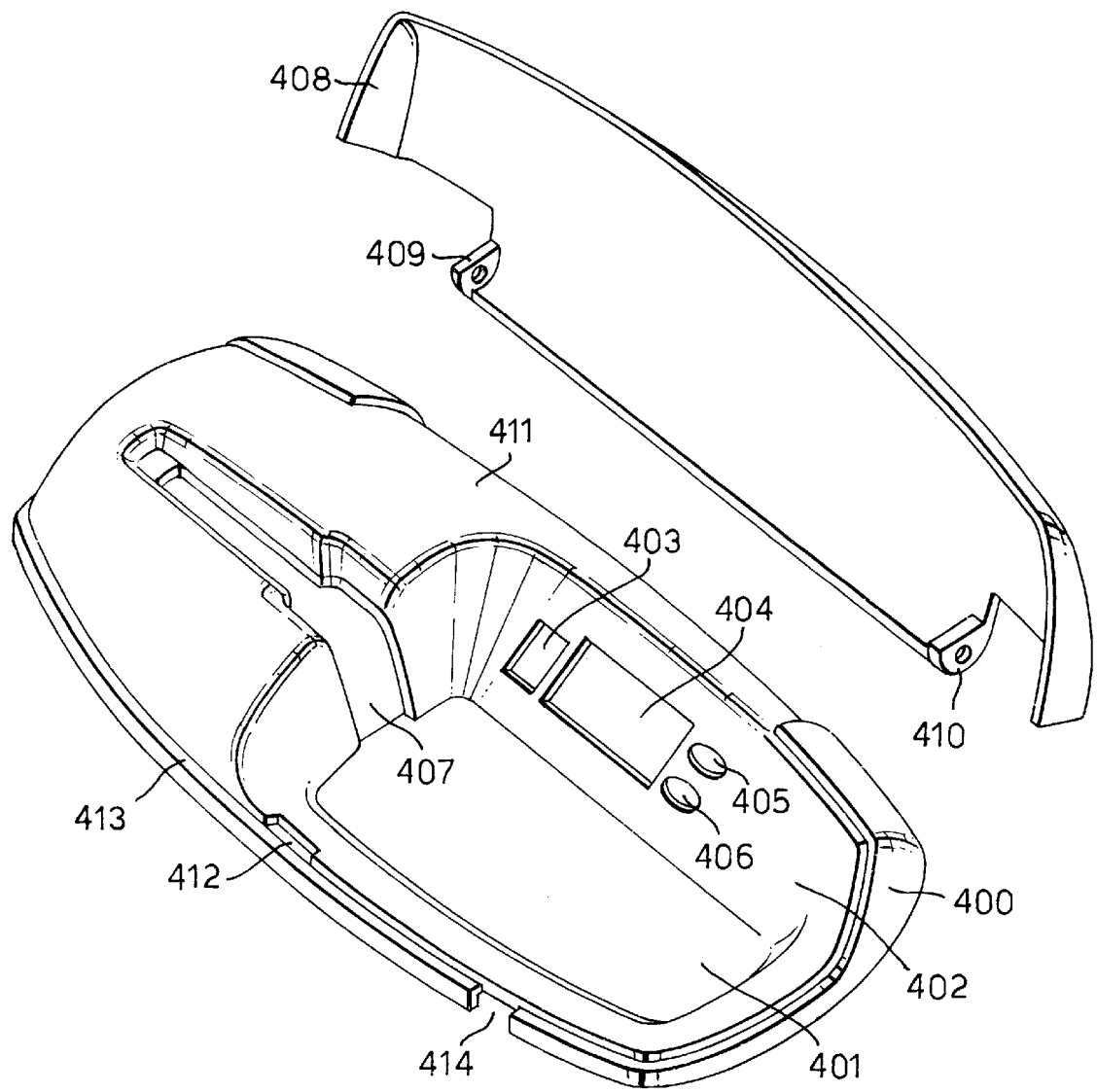

Turning to FIG. 4a, the monitor comprises a moulded casing, eg. of plastic material, having a generally oval rounded shape. The casing principally comprises an upper half 400 and a lower half, only the upper half of which is seen in FIG. 4a. Towards the right hand side of the casing upper half 400 is a recess 401 having a backwardly sloping rear face 402. Rear face 402 incorporates an aperture 403 for a push button (not shown), a window 404 to reveal a display panel (not shown) and two windows 405 and 406 to reveal coloured lights or other indicators (again not shown) to convey information to the user. Extending from the left end of recess 401 is a long slot 407 to provide access to a reading head (not shown) Recess 401 and slot 407 are closable by means of a lid 408 which is attached to the rear of the casing by two hinge points 409 and 410. The upper surface 411 of casing 400 is recessed slightly to accommodate the lid when closed, so that the exterior of the closed device presents a relatively smooth continuous surface to the user. The lid can be flipped up to reveal the user-accessible features of the monitor. The lid is closable by means of a spring clip (not seen in FIG. 4a) which extends upwards through an orifice 412 in the front edge 413 of the casing. Front edge 413 of the casing incorporates a further orifice 414 through which a further indicator light (not shown) may be revealed.

Turning to FIG. 4b, the circuit board 430 is of rounded rectangular shape to match the interior shape of the casing, and carries all of the operational features of the monitor. These include a push button 431 which the user can press to initiate the monitoring of an ovulation cycle. When the circuit board is mounted within the casing and covered by upper half thereof, the push button is accessible through aperture 403. To the right of the push button is a visual display panel 432 such as a liquid crystal display which is visible to the user through window 404. To the right of the display panel are two light guides 433 and 434 which transfer, for example, coloured light (such as red and green) from two LEDs or similar lamps (not shown). Appropriate "chips" and memory circuits 435, 436 are mounted on the circuit board. A further light guide 437 mounted at the front edge 438 of the circuit board can convey light from another LED (not shown) to aperture 414. This light may indicate, for example, to the user that an assay is required. This light can be a different colour from the lights associated with display panel, eg. yellow. A battery connector 439 hangs from beneath the circuit board for connection to batteries retained in the lower casing (see FIG. 4c). Also at the front of the circuit board is a switch 440 operable by the spring catch of lid 408.

At the left hand end of the circuit board is mounted the reading head 441 which comprises a central receiving slot 442 to accommodate one end of an assay device (not shown). On the front of receiving slot 442 is an illuminator 443 and immediately opposite at the rear of the slot is an optical sensing system 444 so that light can be passed across the slot (and through a testing device when inserted) and evaluated by the sensor.

Figure 4C:
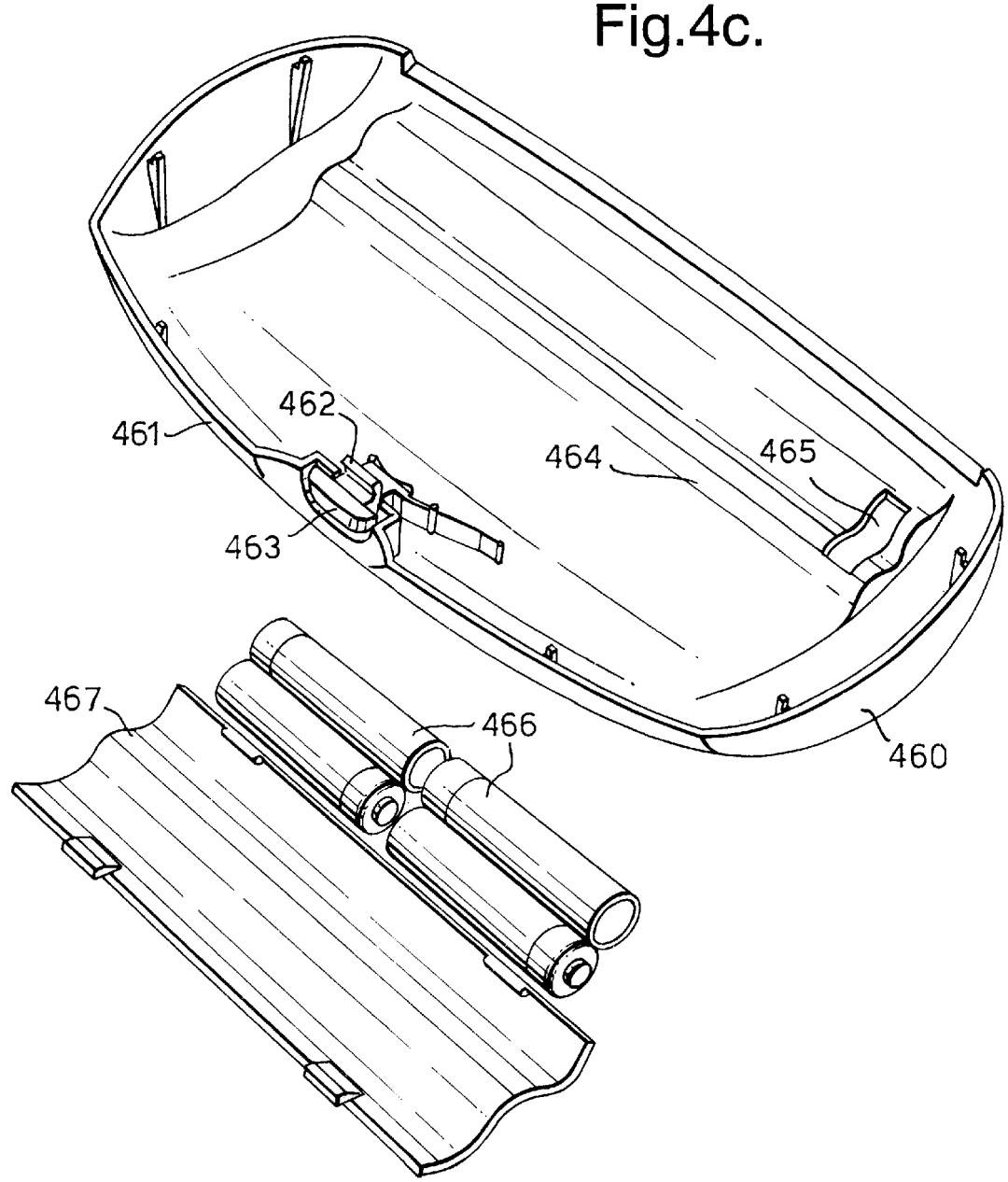

Turning to FIG. 4c, the lower half 460 of the casing has an overall oval shape to match the upper half 400 and provides accommodation for the circuit board 430. The front edge 461 of the casing 460 accommodates a spring loaded catch 462 to fasten lid 408 when closed. Catch 462 is released by pressure on the front face 463 eg. applied by a finger tip. The floor 464 of the casing includes a battery chamber (beneath), and a small access hole 465 is provided towards the right hand end of the casing through which the battery connector 439 can be passed and linked to batteries 466. The batteries are retained by a cover 467 which can be clipped to the underside 468 of the casing.

The constituent parts of the casing can be moulded from high impact or similar plastic materials such as polystyrene and polycarbonate and held together by "push fit" clips or threaded screws or any other appropriate mechanism.

Figure 5:
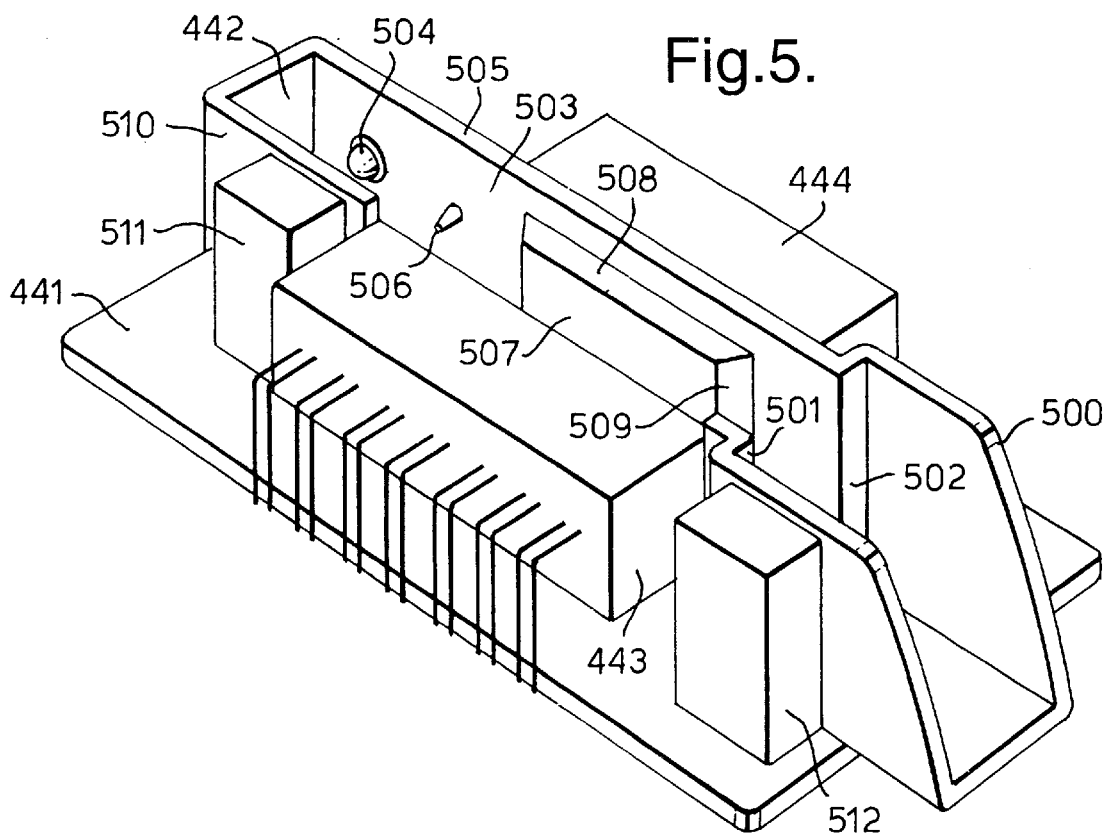
FIG. 5 shows the reading head seen in FIG. 4b on an enlarged scale.

Turning to the enlarged illustration of the reading head, as seen in FIG. 5, the slot 442 for receipt of an assay device is of parallel sided form, but its width is enlarged at its right hand end 500 in a stepped manner to provide a pair of shoulders or abuttments 501, 502 against which a correspondingly enlarged portion of an assay device can be abutted. This can facilitate effective insertion of an assay device into the reading head. Within the narrower working part 503 of the slot is a button 504 mounted on the rear wall 505 of the slot, which must be fully depressed to activate the reading mechanism. Appropriate insertion of a testing device causes adequate depression of this button.

Also on the rear wall 505 of the slot is a fixed locating pin 506 which must engage with a corresponding hole in an inserted assay device. Also on the rear wall 505 is a light-transmitting panel 507 which covers the optical sensors. Panel 507 extends outwardly beyond the plane of rear wall 505 of the slot and has sloping edges 508, 509 to give it a distinctive profile. At opposite ends of the front wall 510 of the slot are two pins (not seen in FIG. 5) which are biased outwardly into the slot, e.g. by spring mechanisms contained within two housings 511, 512.

Figure 6:
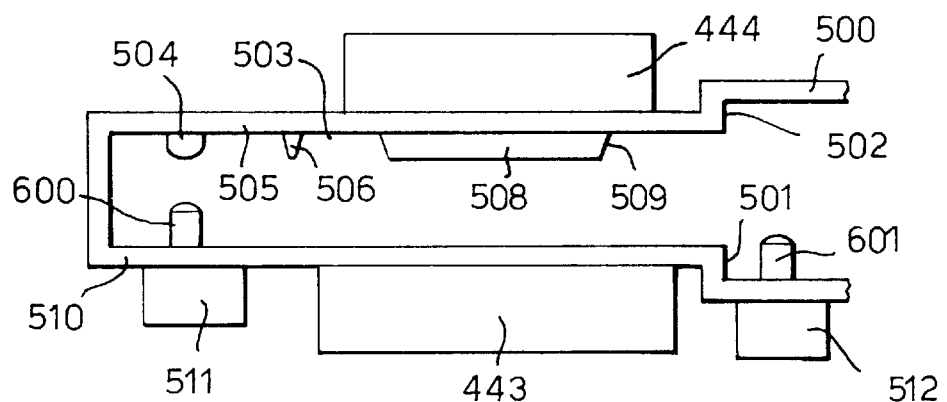
FIG. 6 shows a view directly downwards into the test device receiving slot of the reading head of FIG. 5.

These same features are illustrated in FIG. 6 which is a view directly downwards into the receiving slot. The two biased pins 600, 601 are seen. The purpose of these pins is to provide biasing means to push an inserted assay device against the rear wall 505 of the slot. If the receivable portion of an assay device has appropriately shaped holes or depressions to accommodate the fixed locating pin 506 and the projecting panel 507, the assay device can be pressed sufficiently closely to the rear wall of the slot to depress the button 504 and initiate the optical sensing procedure.

Figure 7:
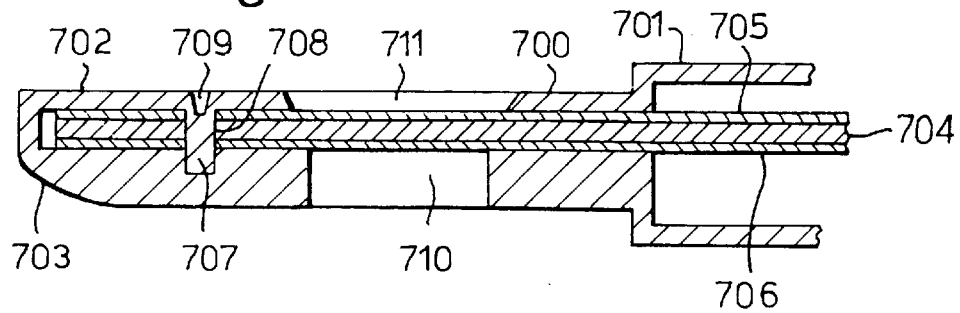
FIG. 7 is a cross-section of one end of a test device designed for insertion into the receiving slot of the reading head.

FIG. 7 shows, in cross-section, part of an assay device 700 having a profile which can cooperate with the features seen in FIG. 6. The assay device can be inserted into the slot with the broader central portion 701 abutting against shoulders 501, 502. The leading end 702 of the assay device has a slightly bevelled edge 703 to facilitate insertion into the slot past pin 600. The assay device comprises a hollow casing containing a porous assay strip 704 sandwiched between two sheets 705, 706 of transparent material. As described earlier, strip 704 is precisely located within the assay device casing by means of a pin 707 which extends through a hole 708 in the strip. On the outside of the assay device casing at a point corresponding to the centre of the locating pin 707 is a conical hole 709 which can accommodate the fixed locating pin 506 in the reader slot. Each side of the assay device casing has an aperture 710, 711 which, when the assay device is inserted in the slot correctly, will be adjacent the light source 443 and light sensors 444 respectively. The profiles of these two apertures are different and in particular the profile of the aperture 711 on the same face of the assay device as the conical hole 709 is shaped to match the profile of the projecting panel 507 covering the light sensors. This ensures that the reading head will only operate when the assay device is inserted in the correct orientation to ensure that the button 504 is depressed.

It will be appreciated that the overall layout and general shape of the monitor can be subject to very considerable variation from that described above without departing from the scope of the invention. The general shape and layout of the reading head is dictated by the need to cooperate effectively with the assay device but this shape can be varied considerably. The layout and nature of the user accessible controls and information display features can likewise be subject to considerable variation and are dictated to a large extent by aesthetic considerations.

The detailed electronics of a monitoring device capable of assimilating, remembering and handling analyte concentration data, as well as providing the preferred electronic features of the device discussed herein, and where appropriate predicting future events, such as the fertility status in an ovulation cycle on the basis of such data, can readily be provided by those skilled in the electronics art once they have been advised of the factors that such a device must take into consideration, and the information that the device must provide for the user. By way of example only, the basic functions that may be required in such a device are outlined in FIG. 8 of the accompanying drawings and described briefly below. The individual features can be entirely conventional, and those familiar with the art of electronics will appreciate that other combinations and arrangements of such features can be employed to achieve the objectives of the invention. For example, so-called "hard-wired" systems, and "neural networks", can be used in place of conventional microprocessors based on "chip" technology.

Figure 8:
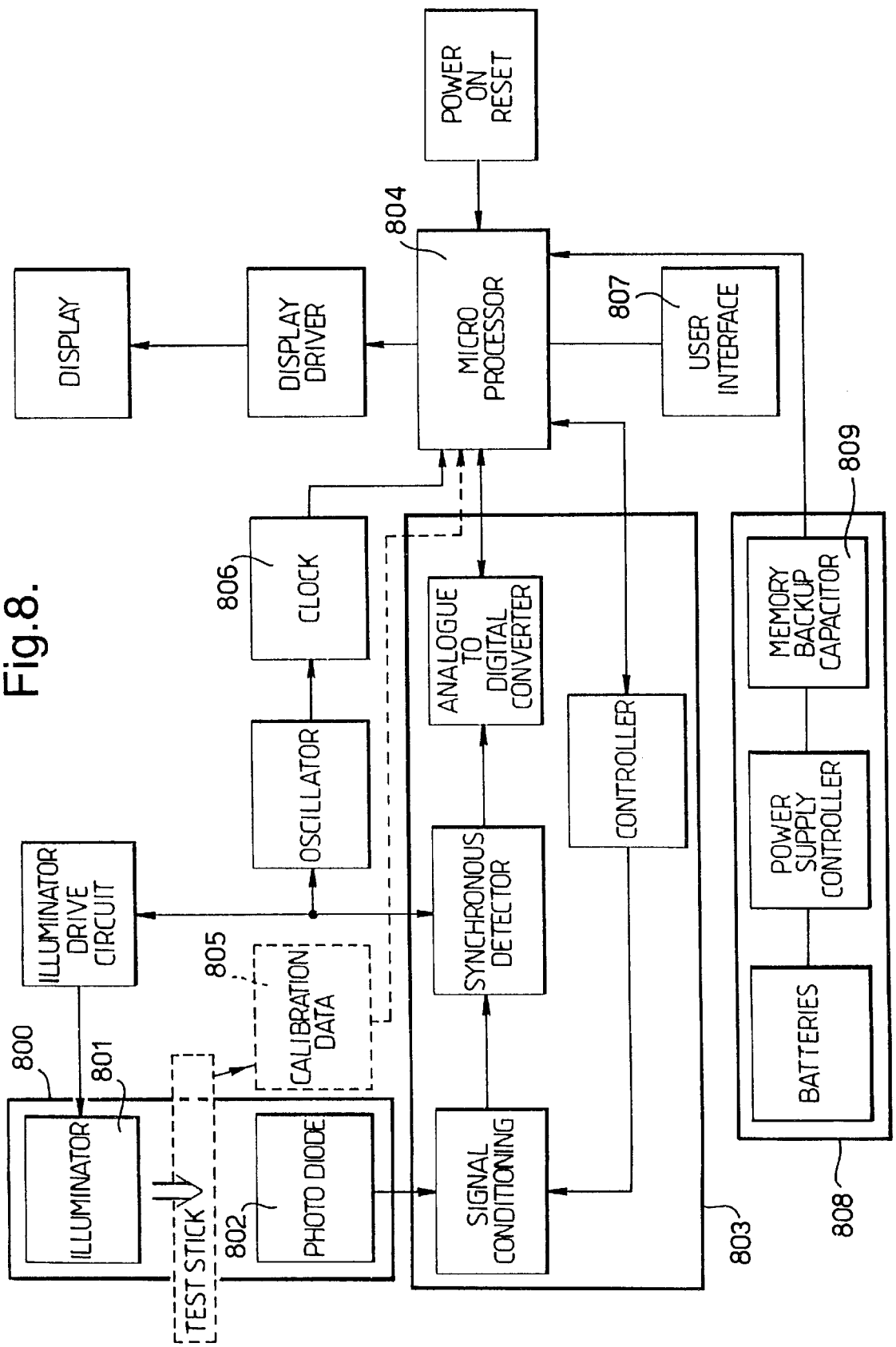
FIG. 8 shows, in schematic form, the basic functions that may be required in an electronic monitor for use in accordance with the invention, as applied to the human ovulation cycle.

As depicted in FIG. 8, the combination essentially comprises a reading unit 800 to derive information from a test device, such as an assay strip, the reading unit comprising an illuminator 801 and a reader 802 (represented here as a photo diode). The reading unit feeds into a conversion unit 803 to convert the optical signal into a form usable by a microprocessor 804. As an optional feature, a calibration system 805 is provided to convert the signal derived from the reading unit into data corresponding, for example, to an absolute concentration value.

A timer, such as a clock 806 may be required to regulate measurements within a cycle. The microprocessor 804 processes, memorizes and interprets results in the light of previous events, particularly recorded from previous cycles. The user interface 807 will generally comprise at least means, such as a push button, which the user can operate at the commencement of a cycle to initiate the operation of the device as a whole. The power supply 808 should include means, such as a memory back-up capacitator 809, to prevent loss of historical data when it becomes necessary to replace batteries.

Information can be conveyed to the user by means of a liquid crystal or LED display, for example. If desired, information on the state of fertility can be conveyed by a 10 simple visual indication, eg a combination of colours showing, for example, green for infertile and red for fertile. Especially if the device is intended primarily as an aid to contraception, it should "fail safe" by showing a "fertile" signal.

As described above, features 803 and 806 together correspond to feature 435 (FIG. 4b), and feature 804 corresponds to feature 436 (FIG. 4b).

Transmission spectrophotometry is a widely used technique for the quantification of dye concentrations in clear liquid solutions. Commercially available spectrophotometers generally require substantial modification to make measurements on diffuse (scattering) solutions. Transmission spectrophotometry is not generally thought of an appropriate method of measuring highly diffuse samples so it is generally only adopted where an alternative approach cannot be applied. For the purposes of the invention, transmission measurement offers positive benefits over the more usual reflectance approach previously employed on test strips.

Some conventional strip assays employ reflectance measurement to assess dye concentration on the strip surface (e.g. glucose monitors). The chemistry of these assays occurs in a very thin layer on the surface of a test strip. In contrast, the chemistry of the preferred strip devices of the invention takes place throughout the thickness of the test strip. Because of variations in flow and reagent deposition, the concentration of detectable label captured at a reaction zone may differ according to depth.

Curvature, surface materials, finish and solvent effects may vary the ratio of specular to diffuse reflection. For reflectance measurements it is the diffusely reflected light from the surface of the strip that carries the signal information (i.e. that light will have interacted with the a detectable label), whilst the specularly reflected light will contain no information (as this light is the component that has just bounced off the surface without interacting with the detectable label in the diffuse strip). Without resorting to relatively bulky and expensive systems, it is difficult to design a reflectance measurement system that minimises specular reflection to the extent possible with transmission measurement, especially using diffuse light as in accordance with the invention.

Reflectance systems require the use of a test surface that must be removed from the optical path for the purposes of calibration. This reference surface must not deteriorate if it is to form a part of the optical assembly. In addition, mechanical movement is required to displace such a reference material when an assay strip needs to be measured. Such problems are avoided by the invention.

In addition to the specific examples of detectable materials already mentioned herein, the invention can use as labels materials which block or reflect the electromagnetic radiation, rather than absorb it, e.g. "white" particles such as latex particles in their natural uncoloured state. Alternatively, the label can be a reactant or catalyst which participates in the generation of a radiation absorbing or radiation-blocking material, e.g. an enzyme which reacts with a substrate to produce a detectable material, such as a coloured material, in the detection zone.

EXAMPLE

The purpose of this example is to confirm that the transmission reading system of the invention enables consistent data to be obtained from a testing device.

A dual-analyte testing device, selected at random from a batch of identical devices constructed as hereinbefore described with reference to FIGS. 1 and 2, using blue-coloured latex particles as a label concentrated in two test lines on a nitrocellulose strip to reveal the test result, was repeatedly inserted and "read" in a monitor constructed as hereinbefore described with reference to FIGS. 3 to 8.

The intensities of the two test lines respectively represented the concentrations of LH and E3G in a urine sample applied to the testing device.

The testing device was inserted and removed from the monitor 10 times. The percentage light transmission for each reading was as follows:

|  | LH | E3G |
|---|---|---|
|  | 44.0 | 39.3 |
|  | 43.8 | 39.3 |
|  | 43.8 | 39.5 |
|  | 43.8 | 39.3 |
|  | 43.8 | 39.3 |
|  | 43.9 | 39.4 |
|  | 43.8 | 39.2 |
|  | 43.9 | 39.2 |
|  | 43.9 | 39.2 |
|  | 43.9 | 39.4 |
| Mean: | 43.9 | 39.3 |
| sd: | 0.1 | 0.1 |
| cv% | 0.2% | 0.3% |

These results indicate that the reading system of the invention produces consistent data which is not affected significantly by any variability of test line placement when the test device is inserted in the monitor.

What is claimed is:

1. An assay result reader, for use in conjunction with an assay device which comprises a porous liquid-permeable carrier in the form of as trip or sheet through the thickness of which electromagnetic radiation is transmissible, said carrier including a detection zone in which an assay result is revealed by specific binding of a detectable material directly or indirectly to a binding agent immobilized in said detection zone, detection of said detectable material being effected by determining the extent to which electromagnetic radiation transmitted through the thickness of said carrier is attenuated by the presence of said detectable material bound in said detection zone, said assay result reader comprising:
   a) receiving means for receiving at least a portion of said assay device, said portion including said detection zone;
   b) reading means associated with said receiving means said reading means comprising:
      (i) at least one source of electromagnetic radiation;
      (ii) one or ore sensors capable of detecting the intensity of said electromagnetic radiation, said source and said one or more sensors being positioned such that when said portion of said assay device is received within said receiving means, said detection zone is disposed in the electromagnetic radiation path between said source and said one or more sensor; and
      (iii) a diffuser in front of said one or more sensors and downstream of said assay device such that electromagnetic radiation from said source must pass through said diffuser before reaching said one or more sensors, said detection zone of said assay device being disposed in the electromagnetic radiation path between said source and said diffuser when said assay device is received within said receiving means.

2. An assay result reader according to claim 1, wherein said electromagnetic radiation is light.

3. An assay result reader according to claim 2, wherein said light is visible light.

4. An assay result reader according to claim 1, wherein said radiation is pulsed and said one or more sensors are synchronized so that they function only in phase with the pulsed radiation.

5. An assay result reader according to claim 4, wherein said radiation has a pulse frequency of at least about 1 kHz.

6. A test kit comprising an assay result reader according to claim 1, together with said assay device comprising a porous liquid-permeable carrier strip or sheet through the thickness of which electromagnetic radiation is transmissible, said carrier including said detection zone in which an assay result is revealed by specific binding of a detectable material directly or indirectly to a binding agent immobilized in said detection zone.

7. A test kit according to claim 6, wherein said assay result reader includes said receiving means for receiving at least a portion of said device, said portion including said detection zone, to present said detection zone to said reading means comprising said electromagnetic radiation and said one or more sensors located such that upon insertion of said device into said receiving means, electromagnetic radiation can be passed through said device and the intensity of electromagnetic radiation emerging from said device can be detected by said one or more sensors.

8. A test kit as claimed in claim 7, wherein said receiving means incorporates interlocking means engageable with corresponding interlocking means on said device to ensure that upon receipt of said device by said reader said at least one detection zone is located and maintained in a predetermined spatial relationship relative to said reading means.

9. A test kit as claimed in claim 8, wherein said receiving means includes actuating means triggered by said receipt of said device, said actuating means causing said reading of said at least one detection zone to be initiated.

10. A test kit according to claim 6, wherein said electromagnetic radiation is light.

11. A test kit according to claim 10, wherein said light is visible light.

12. A test kit as claimed in claim 6, wherein said detectable material comprises a particulate direct label.

13. A test kit as claimed in claim 12, wherein said electromagnetic radiation is visible light of a wavelength that is strongly absorbed by said particulate direct label.

14. A test kit according to claim 6, wherein said assay device is one of a plurality of identical such devices provided as part of the kit.

15. A test kit comprising an assay result reader together with an assay device comprising a porous liquid-permeable carrier in the form of a strip or sheet through the thickness of which electromagnetic radiation is transmissible, said carrier including a detection zone in which an assay result is revealed by specific binding of a detectable material directly or indirectly to a binding agent immobilized in said detection zone, detection of said detectable material being effected by determining the extent to which electromagnetic radiation transmitted through the thickness of said carrier is attenuated by the presence of said detectable material bound in said detection zone, said assay result reader comprising:

a) receiving means for receiving at least a portion of said assay device, said portion including said detection zone:

b) reading means associated with said receiving means, said reading means comprising:
      (i) at least one source of electromagnetic radiation; and
      (ii) one or more sensors capable of detecting the intensity of said electromagnetic radiation, said source and said one or more sensors being positioned such that when said portion of said assay device is received within said receiving means, said detection zone is disposed in the electromagnetic radiation path between said source and said one or more sensors; and
      (iii) a diffuser in front of said one or more sensors such that electromagnetic radiation from said source must pass through said diffuser before reaching said one or more sensors said detection zone of said assay device being disposed in the electromagnetic radiation path between said source and said diffuser when said assay device is received within said receiving means and wherein said carrier of said assay device is within a casing or cover forming part of said assay device, and said casing or cover having electromagnetic energy transmitting regions enabling electromagnetic radiation to be passed through said device, said detection zone lying in the electromagnetic radiation path between said transmitting regions.

16. A test kit as claimed in claim 15, wherein said device casing or cover includes internal registration means which engages with corresponding registration means associated with said carrier such that said detection zone within said device casing or cover is located in a predetermined spatial relationship relative to interlocking means on said device casing or cover.

17. A test kit according to claim 16, wherein said internal registration means comprises a pin or the like, engageable with a hole or indentation in said carrier, said detection zone being at a predetermined location on said carrier relative to said hole or indentation.

18. A test kit according to claim 15, wherein said electromagnetic radiation from said source is pulsed.

19. A test kit comprising an assay result reader together with an assay device comprising a porous liquid-permeable carrier in the form of a strip or sheet through the thickness of which electromagnetic radiation is transmissible, said carrier including a detection zone in which an assay result is revealed by specific binding of a detectable material directly or indirectly to a binding agent immobilized in said detection zone, detection of said detectable material being effected by determining the extent to which electromagnetic radiation transmitted through the thickness of said carrier is attenuated by the presence of said detectable material bound in said detection zone, said assay result reader comprising:

a) receiving means for receiving at least a portion of said assay device, said portion including said detection zone;

b) reading means associated with said receiving means, said reading means comprising:
      (i) at least one source of diffuse electromagnetic radiation; and
      (ii) one or more sensors capable of detecting the intensity of said electromagnetic radiation, said source and said one or more sensors being positioned such that when said portion of said assay device is received within said receiving means, said detection zone is disposed in the electromagnetic radiation path between said source and said one or more sensors; and
      (iii) a diffuser in front of said one or more sensors such that electromagnetic radiation from said source must pass through said diffuser before reaching said one or more sensors, said detection zone of said assay device being disposed in the electromagnetic radiation path between said source and said diffuser when said assay device is received within said receiving means wherein said carrier strip or sheet comprises nitrocellulose having a thickness not exceeding 1 mm.

* * * * *